(12) United States Patent
Bergey (10) Patent No.: US 10,898,345 B2
(45) Date of Patent: Jan. 26, 2021

(54) COMPOUND-ARC, SPLINED ANCHOR

(71) Applicant: Darren L. Bergey, Riverside, CA (US)

(72) Inventor: Darren L. Bergey, Riverside, CA (US)

(*) Notice: Subject to any disclaimer, the term of this patent is extended or adjusted under 35 U.S.C. 154(b) by 178 days.

(21) Appl. No.: 16/263,405

(22) Filed: Jan. 31, 2019

(65) Prior Publication Data

US 2019/0224019 A1    Jul. 25, 2019

Related U.S. Application Data

(60) Division of application No. 15/380,048, filed on Dec. 15, 2016, now Pat. No. 10,195,051, which is a
(Continued)

(51) Int. Cl.
*A61F 2/44* (2006.01)
*A61F 2/30* (2006.01)
*A61F 2/28* (2006.01)

(52) U.S. Cl.
CPC ............ *A61F 2/447* (2013.01); *A61F 2/4425* (2013.01); *A61F 2/4455* (2013.01); *A61F 2/4465* (2013.01); *A61F 2002/2817* (2013.01); *A61F 2002/2835* (2013.01); *A61F 2002/3023* (2013.01); *A61F 2002/30187* (2013.01); *A61F 2002/30578* (2013.01); *A61F 2002/30593* (2013.01); *A61F 2002/30607* (2013.01); *A61F 2002/30616* (2013.01); *A61F 2002/30782* (2013.01);
(Continued)

(58) Field of Classification Search
CPC ............ A61F 2/447; A61F 2002/30841; F16B 15/06; A61B 17/846
See application file for complete search history.

(56) References Cited

U.S. PATENT DOCUMENTS 1,635,923 A    7/1927   Bray
6,128,867 A   10/2000   MacKarvich
(Continued)

FOREIGN PATENT DOCUMENTS

CA    2758922 A1    10/2010
CN    1244105 A     2/2000
(Continued)

OTHER PUBLICATIONS

American Society for Reproductive Medicine, Adhesion Prevention: A Standard of Care, Surgical Techniques and Cost Effectiveness of Adhesion Prevention, Aug. 20, 2014.
(Continued)

*Primary Examiner* — Andrew Yang
(74) *Attorney, Agent, or Firm* — Pate Baird, PLLC (57) ABSTRACT

An intervertebral implant includes a body and a plate. The body has an upper surface defining an upper plane and a lower surface defining a lower plane. First and second fastener holes of the plate are configured to retain the heads of first and second fasteners. A portion of each of the shanks of the first and second fasteners extends from the first and second fastener holes beyond the upper plane. The shank portions of the first and second fasteners are curved in a direction away from the upper surface. The third fastener hole is configured to retain the head of the third fastener between the upper and lower planes. A portion of the shank of the third fastener extends from the third fastener hole beyond the lower plane. The shank portion of the third fastener is curved in a direction away from the lower surface.

20 Claims, 3 Drawing Sheets

Related U.S. Application Data division of application No. 15/001,502, filed on Jan. 20, 2016, now Pat. No. 9,539,110, which is a division of application No. 13/937,208, filed on Jul. 8, 2013, now Pat. No. 9,248,029, which is a continuation of application No. PCT/US2012/020560, filed on Jan. 6, 2012.

(60) Provisional application No. 61/430,296, filed on Jan. 6, 2011.

(52) U.S. Cl.
CPC ............ *A61F 2002/30787* (2013.01); *A61F 2002/30841* (2013.01); *A61F 2002/30878* (2013.01); *A61F 2002/30904* (2013.01); *A61F 2310/00023* (2013.01); *A61F 2310/00161* (2013.01)

(56) References Cited

U.S. PATENT DOCUMENTS

| | | |
|---|---|---|
| 6,432,106 B1 | 8/2002 | Fraser |
| 8,142,508 B1 | 3/2012 | Bruffey et al. |
| 8,167,949 B2 | 5/2012 | Tyber et al. |
| 8,267,997 B2 | 9/2012 | Colleran |
| 8,292,958 B1 | 10/2012 | Bruffey et al. |
| 8,353,938 B2 | 1/2013 | Trieu et al. |
| 8,366,774 B1 | 2/2013 | Bruffey et al. |
| 8,414,651 B2 | 4/2013 | Tyber et al. |
| 8,460,294 B2 | 6/2013 | Overes |
| 8,500,784 B2 | 8/2013 | Hulliger et al. |
| 8,506,534 B2 | 8/2013 | Marnay et al. |
| 8,523,916 B2 | 9/2013 | Anderson et al. |
| 8,568,483 B2 | 10/2013 | Coppes et al. |
| 8,579,903 B2 | 11/2013 | Carl |
| 8,579,978 B2 | 11/2013 | Marnay et al. |
| 8,591,513 B2 | 11/2013 | Overes et al. |
| 8,603,144 B2 | 12/2013 | Kwak et al. |
| 8,617,225 B2 | 12/2013 | McShane et al. |
| 8,623,057 B2 | 1/2014 | Jahng et al. |
| 8,641,734 B2 | 2/2014 | Moumene et al. |
| 8,641,766 B2 | 2/2014 | Donner et al. |
| 8,647,347 B2 | 2/2014 | Runco et al. |
| 8,663,229 B2 | 3/2014 | Marnay et al. |
| 8,663,292 B2 | 3/2014 | Dec et al. |
| 8,663,298 B2 | 3/2014 | Keyer et al. |
| 8,679,162 B2 | 3/2014 | Strausbaugh et al. |
| 8,685,066 B2 | 4/2014 | Stad et al. |
| 8,685,104 B2 | 4/2014 | Lee et al. |
| 8,696,703 B2 | 4/2014 | Anspach, III et al. |
| 8,721,692 B2 | 5/2014 | Anderson et al. |
| 8,734,490 B2 | 5/2014 | Anderson et al. |
| 8,740,946 B2 | 6/2014 | Peterson et al. |
| 8,757,035 B2 | 6/2014 | Kerboul et al. |
| 8,771,271 B2 | 7/2014 | Overes |
| 8,777,960 B2 | 7/2014 | Murray et al. |
| 8,795,371 B2 | 8/2014 | Marnay et al. |
| 8,828,007 B2 | 9/2014 | Stad et al. |
| 8,845,697 B2 | 9/2014 | Montello et al. |
| 8,845,700 B2 | 9/2014 | Kwak et al. |
| 2006/0085071 A1 | 4/2006 | Lechmann |
| 2011/0098747 A1 | 4/2011 | Donner et al. |

FOREIGN PATENT DOCUMENTS

| | | |
|---|---|---|
| CN | 101442944 B | 5/2009 |
| EP | 0427906 A1 | 5/1991 |
| EP | 2361573 A2 | 8/2011 |

OTHER PUBLICATIONS

SprayShield.org, Informations about adhesions barriers and SprayShield Adhesion barrier, the new product by Covidien, Oct. 2011.
Women's Surgery Group, Adhesion Overview, Aug. 21, 2014.
The American Journal of Surgery, Peritoneal adhesions and their relation to abdominal surgery, vol. 126, Issue 3, pp. 345-353, Sep. 1973.
British Journal of Surgery Society Ltd, Morbidity and mortality of inadvertent enterotomy during adhesiotomy, vol. 87, Issue 4, Apr. 2000, published online Dec. 6, 2002.
American Academy of Orthopaedic Surgeons, Choosing Wisely, An initiative of the ABIM Foundation, Sep. 11, 2013.
Human Reproduction Update, Clinical implications of postsurgical adhesions, vol. 7, No. 6, pp. 567-576, 2001.
The Lancet, Adhesion-related hospital readmissions after abdominal and pelvic surgery: a retrospective cohort study, vol. 353, Issue 9163, pp. 1476-1480, 1999.
PubMed NCBI, Peritoneal adhesions; etiology, pathophysiology, and clinical significance. Recent advances in prevention and management Dig. Surg. 2001; 18(4):260-73.
MedicineNet.com, Abdominal Adhesions (Scar Tissue), Aug. 20, 2014.
Better Health Channel, Fact Sheet, Adhesions, Aug. 20, 2014.
Journal of Surgical Research, Heated and Humidified CO, Prevents Hypothermia, Peritoneal Injury, and Intra-Abdominal Adhesions During Prolonged Laparoscopic Insufflations, vol. 152, Issue 1, pp. 40-47, Jan. 2009, published online May 12, 2008.
Oxford Journals, Medicine and Health, Human Reproduction Update, vol. 19, Issue 1, pp. 12-25, Jan./Feb. 2013, published online Aug. 16, 2012.
Synechion, Inc., Adhesions Related Disease-Adhesions Related Deaths, Sep. 23, 2003.
PubMed NCBI, Histologic study of peritoneal adhesions in children and in rate model, Pediatr Surg Int. Dec. 2002; 18(8):676-6, Epub Sep. 24, 2002.
Human Reproduction Update, Peritoneal repair and post-surgical adhesion formation, vol. 7, No. 6, pp. 547-555, 2001.

COMPOUND-ARC, SPLINED ANCHOR

RELATED APPLICATIONS

This application: is a divisional application of U.S. patent application Ser. No. 15/380,048, filed Dec. 15, 2016, and due to issue Feb. 5, 2019 as U.S. Pat. No. 10,195,051; which is a divisional application of U.S. patent application Ser. No. 15/001,502, filed Jan. 20, 2016, issued as U.S. Pat. No. 9,539,110 on Jan. 10, 2017; which is a divisional application of U.S. patent application Ser. No. 13/937,208, filed Jul. 8, 2013, issued as U.S. Pat. No. 9,248,029 on Feb. 2, 2016; which is a continuation of PCT Application Serial No. PCT/US2012/020560, filed Jan. 6, 2012; which claims the benefit of U.S. Provisional Patent Application Ser. No. 61/430,296, filed Jan. 6, 2011. All the foregoing references are hereby incorporated herein by reference.

BACKGROUND

Field of the Invention

The present invention relates to implantable intervertebral implants and fasteners particularly useful for assisting with the surgical arthrodesis (fusion) of two spinal vertebrae and more particularly, to an anchoring system that provides and controls limited movement between vertebrae during fusion.

Background Art

Various genetic or developmental disorders can affect the structure and function of the spinal column. Trauma or advancing age can lead to changes in the bones, disks, joints, and ligaments of the spine producing pain. Under certain circumstances, alleviation of pain can be provided by performing a spinal arthrodesis, commonly known as a spinal fusion. This procedure is accepted and performed by the spinal community and involves joining two or more adjacent vertebrae so that they are no longer able to move relative to each other.

Many prosthetic devices are known for promoting fusion of the spinal vertebrae. The spine surgical community has accepted intervertebral devices—commonly known as interbody spacers—as part of the state of the art and routine practice employs such devices for spinal arthrodesis. Surgeons insert these intervertebral devices to facilitate bone fusion in between and into the contiguous involved vertebrae. This fusion creates a new solid bone mass, which acts to hold the spinal segment at an appropriate biomechanically restored height as well as to stop motion in a segment of the spine in which the patient is experiencing pain. Items surgically placed in these involved interbody regions can thus stimulate interbody bone in-growth such that the operated anterior spinal segments heal into a contiguous bone mass; in other words, a fusion occurs.

These prosthetic devices may be classified, in part, based upon the approach to the spine through which they will be inserted (anterior, lateral, posterior, etc). They may also be classified based upon their mechanism of spinal fixation (separate plate and screw fixation, incorporated blade/screw fixation, incorporated screw fixation without plate, blade fixation without plate). When referenced throughout this disclosure, the term "blade" can be considered to include a blade, a nail, an anchor, and/or a non-threaded screw.

There are several commercially available devices that operate as stand-alone (that is, without support from an additional construct such as an anterior plate and screws, or posteriorly placed screws and/or rods placed into the pedicles or facet joints) interbody fusion devices. These devices include the Stalif™, SynFix™, Zero-P™, and the VerteBridge™. The Stalif™ is a device for the fusion of the lumbar spine. The implant is inserted and fixed via diverging screws passing through pre-drilled apertures of the device that penetrate into the vertebral bodies without the use of a plate or locking of the screws. The screws are manually placed into the apertures of the device and are driven using an appropriate tool, such as a surgical screw driver. The SynFix™ is also a device for fusion of the lumbar spine that is placed in an intervertebral space and fixed via diverging screws passing through the device and into the vertebral bodies. Again, the screws are manually placed into the apertures of the device and are driven using a surgical screw driver. The Zero-P™ is a cervical fusion device which also fixed via diverging screws passing through the device and into the vertebral bodies. Again, the screws are manually placed into the apertures of the device and are driven using a surgical screw driver. The VerteBridge™ is a device for the fusion of the cervical or lumbar spine in which anchoring blades are press-driven through apertures in the device and into the respective vertebral bodies to fix the device in place without the use of a plate.

All of the above-described devices have an anchor which is secondarily added to the initial device. The Stalif™, SynFix™, and Zero-P™ devices employ screws while the VerteBridge™ utilizes a blade anchor. Both the Stalif™ and SynFix™ devices require the screws to be inserted at trajectories that are difficult to achieve given common human anatomical structures, especially at the spinal level L5-S1. Additionally, the proximal end of the screws may protrude anteriorly, causing potential irritation to the great vessels overlying the lumbar spine. Due to the problematic angulation of the screw trajectory, hinged screw drivers are provided for their insertion. These difficult trajectories increase the difficulty of insertion and increase the risk of injury to surrounding structures. Rigid fixation through the SynFix™ or the Zero-P™ does not allow for the interbody graft to heal in compression which increases the chance of pseudoarthrosis (failure of fusion). The VerteBridge™ has a pair of blades inserted after the initial device is put in place. These blades have a locking mechanism which cannot be released if removal of the implant is required. The locking mechanism is supposed to be of sufficient strength to prevent failure and backout of the anchor to prevent irritation or injury to the great vessels overlying the lumbar spine or the esophagus overlying the cervical spine. Additionally, the blade anchors are supposed to exhibit sufficient biomechanics to allow appropriate segmental immobilization to promote solid arthrodesis. In practice, these features are not always achieved.

There are several commercially available devices that operate as anchoring devices placed in a direct lateral position in the lumbar spine. The XLP™, the ORACLE™, and the ZUMA™ employ a plate and screws to stabilize the anterior spine when an intervertebral device is placed through a direct lateral transpsoas approach to the lumbar spine. These fixation devices are placed over the lateral vertebral body and have the disadvantage of risk to the traversing nerve roots which pass through this region. The ORACLE™ and ZUMA™ plating systems employ a four-hole plate for fixation and the width of the plate makes safe placement through this lateral region of the spine difficult. The XLP™ is a two-hole plate that minimizes this risk but the plating system also encroaches on these traversing nerve roots. There currently is no stand-alone interbody fusion device that provides direct lateral lumbar fusion with biomechanical fixation while still protecting the nerve roots through this approach.

Further conventional devices are described by Donner/Synthes (4-2009) wherein an Arcuate Fixation Member is described. Despite the accurate description of a curvalinear anchor with multiple fixation purposes, the described device is lacking in several areas as it relates to interbody fusion. First and foremost, the broad description of the arcuate anchor lacks critical specifications. Relative to interbody fusions, regardless of whether the anchor is curvilinear in a continuous or noncontiguous fashion, the final angulation relative to the horizontal plane may be critical. If the resulting angulation is not within 50-90 of the horizontal plane, the device cannot be expected to improve that currently available. Further, the mating boring guide will loosen the anchor and its fixation from the outset, and the tapered shaft will decrease bone surface area contact and fixation. The device also lacks guiding splines on the blades with a matching portal through the fixation plate for reproducible accurate blade placement. Absent also is a top loading introducer for matching the portal through the plate to overcome the current difficulty with screw trajectory. This is perhaps the most important aspect as patient safety is at risk with the use of hinged screwdrivers, drills, and awls. Thus, the arcuate fixation member will fail to overcome the problems inherent with the current devices available.

It may be desirable to provide an intervertebral device for the fusion of the cervical or lumbar spine in which anchoring blades are placed through apertures in the device and into the respective vertebral bodies to fix the device in place with the use of a plate. This device would utilize helical or non-helical angled blades which are locked to a plating system to prevent back-out and risk to the great vessels overlying the lumbar spine, and prevent risk to the esophagus overlying the cervical spine. This plate would also avoid risk to the traversing nerve roots through the direct lateral or transpsoas approach to the lumbar spine. This anchoring system may have the benefit of functioning as a stand-alone intervertebral device or as a separate plating device by itself. This intervertebral device would allow for safe removal if necessary. This device would also overcome the problems encountered with the current art requiring screws to be inserted at trajectories that are difficult to achieve given common human anatomical structures and would not require insertion with screw drivers or hinged screw drivers. This device would also allow fusion segments to heal in compression, allowing for increased fusion rates as a result of the blade design.

It may be desire to provide an intervertebral device that would utilize angled blades with either linear or helical spiines. The curvalinear radius of the splined blade anchor may result in a terminal angulation of 50-90 degrees as measured from the horizontal plane. This feature is disregarded in the prior art ignoring Wolfs law which states that bone heals best in compression. It may be further desirable to provide a device without a slidabably mating curved guiding bore through which the curved anchor is inserted, as this may cause the curved bone anchor to be inserted loosely. There will instead be no need for this as the configuration of the splined blade and its mated portal through the fixation plate will guide the anchor to its ideal position without compromising tight fixation.

It may be desirable to provide a device with a minimum of two fixation blades, and in some aspect preferably three. This may afford more adequate biomechanical fixation and allow use at multiple consecutive vertebral levels as well as levels above or below previously instrumented vertebral segments. Superior and inferior Blades will be oriented in a directly opposing manner as referenced from the horizontal plane optimizing compressive subsidence of vertebral segments.

It may be desirable to provide a device with a minimum of two splines orientated in either a linear or helical fashion with respect to the longitudinal axis of the blade whose purpose is to guide the blade accurately to its correct position within the bone. There may be no taper between the proximal and distal ends allowing for larger contiguous surface area for bone fixation. The head or proximal end of the blade may have the same spline orientation as the shaft so there will be no change in course throughout the entire length of the blades insertion through bone. The proximal end and head may not only have same spline orientation but may also have a morse taper matching the guiding chamber of the plate. The proximal end, head, with the features above, may seat into the plate such that the spines would be below the anterior surface of the plate allowing for a single cover screw to prevent backout if the morse taper was felt to be inadequate.

BRIEF SUMMARY OF THE INVENTION

Embodiments of the present invention are stand-alone interbody devices, which may be designed in the general style of an anterior lumbar interbody fusion (ALIF) device, a transforaminal lumbar interbody fusion (TLIF) device, a posterior lumbar interbody fusion (PLIF) device, an extreme lateral or direct lateral interbody device fusion device, or an anterior cervical interbody fusion device.

The device includes a body made from any variety of structural biomaterial including, but not limited to, polyetheretherketone (PEEK), Titanium, carbon fiber, ceramic, etc. The body may have serrated superior and/or inferior surfaces to provide initial resistance against migration. Additionally, there may be at least one opening extending from the superior surface to the inferior surface for the purpose of containing osteo-inductive, osteo-conductive material, such as autograft, bone morphogenetic protein (BMP), or one of a variety of bone graft substitutes as is the accepted practice in the spinal community.

According to various aspects of the disclosure, an intervertebral implant may include the above mentioned body and a plate associated with the body. The plate may be mated with the body prior to insertion or may be modular in that it may be attached after the body is inserted into the intervertebral space. The plate may be implanted independently from the body of the device. The plate may be inserted to fit inside the interbody space completely or level with the anterior surface of the vertebral body so as not to interfere with the great vessels lying over the lumbar spine or the esophagus anterior to the cervical spine. The plate may be inserted to fit inside the interbody space completely or level with the lateral surface of the vertebral body so as not to interfere with the nerve roots when inserted through a direct lateral lumbar approach.

The plate includes at least a superior and inferior fastener hole. Additional fastener holes may be included dependent on the spinal segment being addressed for fusion. At least a third fastener hole is envisioned when utilized within the anterior lumbar spine for biomechanical stability.

The implant includes at least superior and inferior fasteners each having a head and a shank. The first and second fastener holes may be configured to retain the heads of the first and second fasteners respectively between the upper and lower planes. A portion of each of the shanks of the first and second fasteners extends from the first and second fastener holes respectively beyond the upper plane.

The shank portions of the first and second fasteners may be curved in a direction away from the upper surface of the body. This angular feature allows for insertion of the fastener through a unique top loading approach through the plate. This unique feature overcomes the problems encountered with the current art requiring screws to be inserted at trajectories that are difficult to achieve given common human anatomical structures and would not require insertion with screw drivers or hinged screw drivers.

The third fastener hole may be configured to retain the head of the third fastener between the upper and lower planes. A portion of the shank of the third fastener extends from the third fastener hole beyond the upper plane. The shank portion of the third fastener may be curved in a direction away from the upper surface of the body.

In accordance with some aspects of the disclosure, a fastener for an intervertebral implant may include a head portion and a shank portion extending from the head portion. The shank portion may have a substantially circular cross section adjacent the head portion and a flattened free end opposite the head portion. The shank portion transitions from the circular cross section to the flattened free end in a substantially continuous manner. At least one spine may be arranged helically on the shank portion. The spine may extend from the circular cross section to the flattened free end.

One of the benefits of the embodiments of the invention is the ease with which the device may be used. There are fewer steps as compared with conventional devices because there are no screws to be inserted and the spiral blades can be inserted, through the same device used for insertion of the plate, in a top loading fashion. Furthermore, because the spiral blades are angled relative to the intervertebral plane, there is no difficult trajectory needed to place the screws as with previous devices. As opposed to devices employing blades without plate fixation, the embodiments of the invention employ spiral blades affixed to a rigid plate, which provide better fixation, stabilization, and the ability to remove this device without destruction of the vertebral anatomy if required.

Some further advantages and embodiments may become evident from the attached drawings.

BRIEF DESCRIPTION OF THE DRAWINGS

The invention will be more fully understood from the following detailed description taken in.

DETAILED DESCRIPTION OF THE PREFERRED EMBODIMENTS

Figure 1:
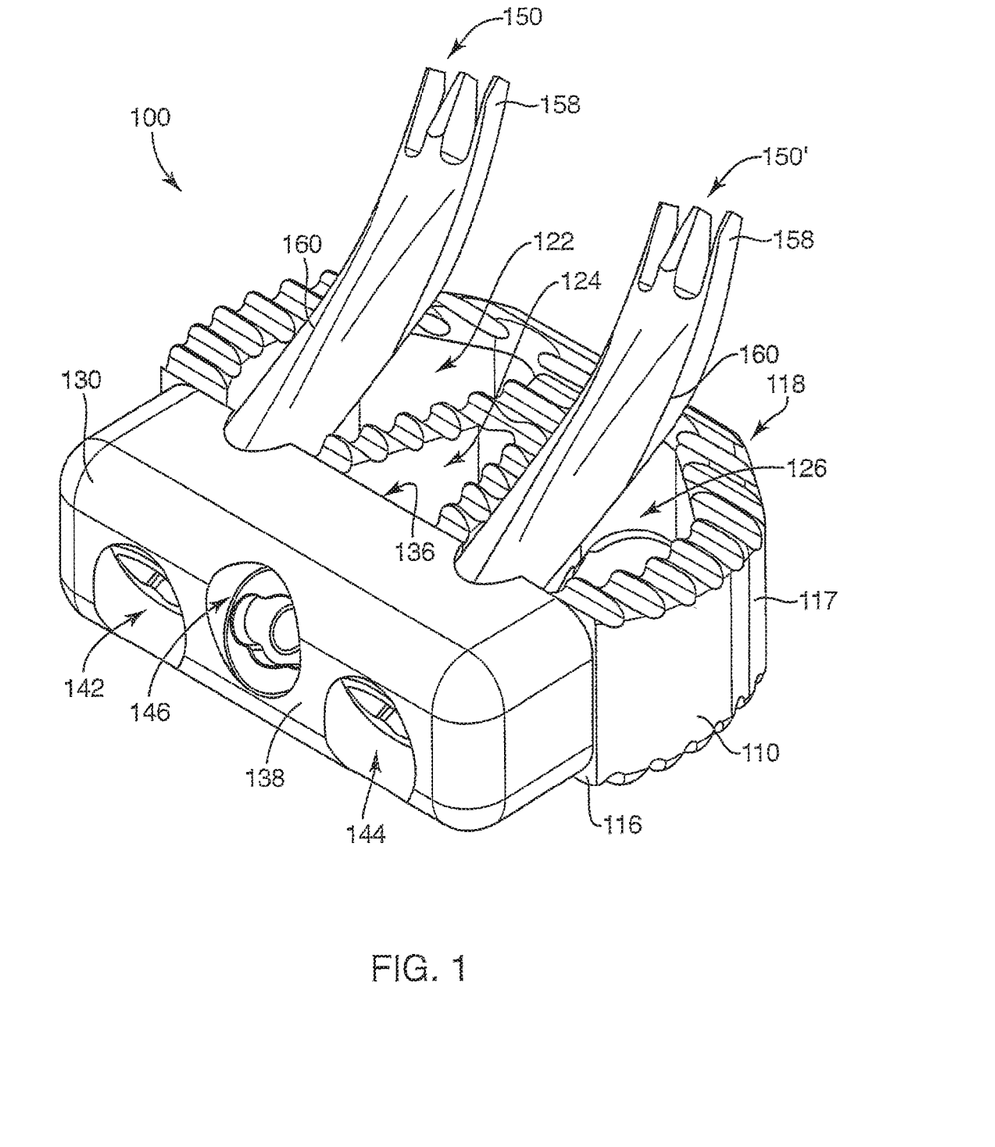
FIG. 1 is a top perspective view of an exemplary intervertebral implant in accordance with various aspects of the disclosure.
Figure 2:
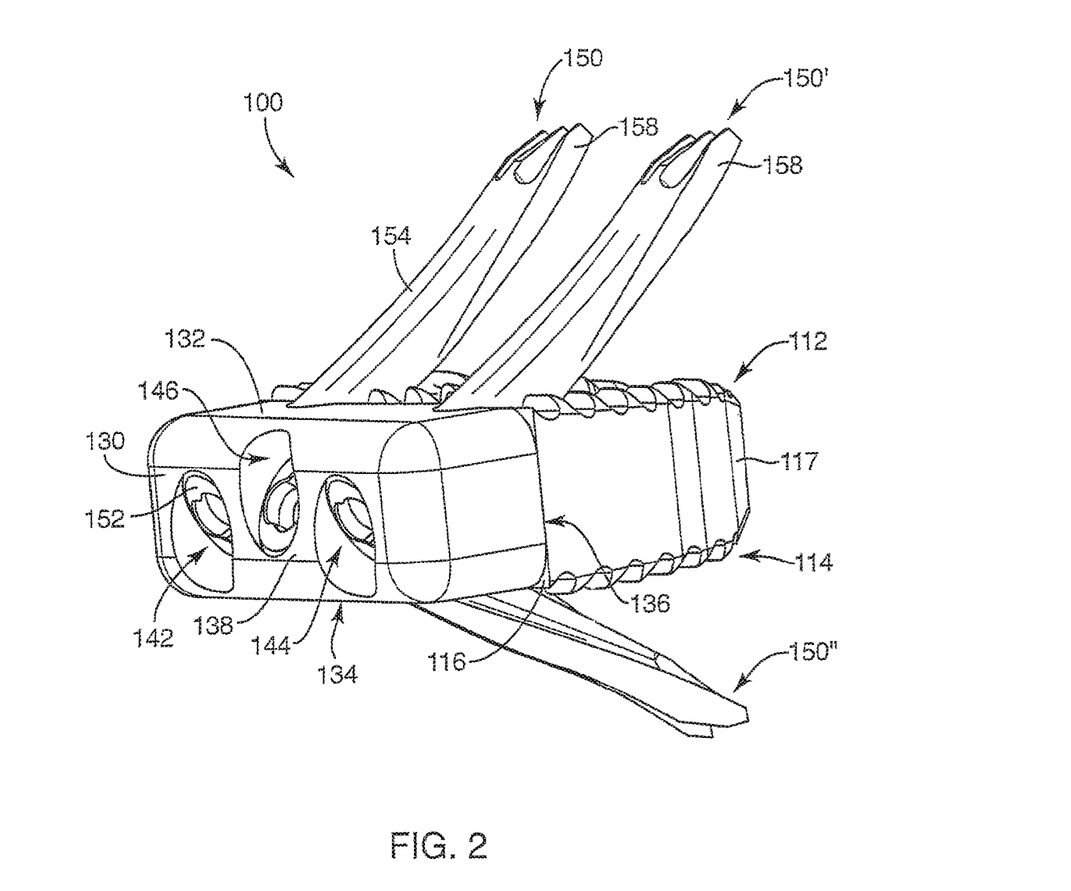
FIG. 2 is a front perspective view of an exemplary intervertebral implant in accordance with various aspects of the disclosure.

FIGS. 1 and 2 illustrate an exemplary intervertebral implant 100 in accordance with the disclosure. An intervertebral implant 100 generally includes a body (or housing) that is sized and shaped to fit in the intervertebral space between adjacent vertebral bones (not shown) of the human spine. It is understood that the size and shape of the device 100 may be adapted to fit in an intervertebral space at any level of the spine, such as the cervical spine, thoracic spine, or lumbar spine. The intervertebral device 100 as illustrated in this example is designed to be a stand-alone device, having a plate 130 attached through a locked or modular attachment (e.g., requiring no separate anchoring devices), which is inserted into the inter-vertebral space from an anterior direction. This embodiment is in the general form of an ALIF device, although as will be appreciated from the description herein, the device may be adapted to operate as an extreme lateral or direct lateral interbody device, an anterior cervical interbody device, or a TLIF or PLIF device.

The body 110 has an upper surface 112 defining an upper plane and a lower surface 114 defining a lower plane. The body 110 also includes a horizontal center plane intermediate the upper and lower surfaces 112, 114 and substantially parallel to the upper and lower planes defining a longitudinal axis. With reference to FIGS. 1 and 2, it is understood that the longitudinal axis may not be precisely normal to the first and second major surfaces 112, 114 as there may be a slight narrowing height (taper) to the body from the anterior sidewall 116 to the posterior sidewall 118. This taper is designed to accommodate the natural anatomic relationships between the adjacent vertebral bones, thereby maintaining the normal lordodic curvature of the spine.

The body 110 may include a plurality of cutouts 122, 124, 126 extending through the body 110 from the upper surface 112 to the lower surface 114. These cutouts are used to provide the trajectory of the fasteners. According to various aspects, the body 110 may be comprised of polyetheretherketone (PEEK) or other radiolucent material, such as a carbon fiber composite, which is well suited for fabrication of the body.

According to various aspects, the upper and lower surfaces may be designed to rest against the end plates of two adjacent vertebrae and/or against upper or lower surfaces of another implant 100. To achieve improved anchoring, the upper and lower surfaces 112, 114 may be topographically shaped and/or may be fitted with gripping members 116, such as for example, serrations, grooves, ribs, or teeth, or their surfaces may be roughened in any known manner. In some aspects, the body 110 may include one or more sidewalls 117. The sidewalls 117 may include gripping members 120 (e.g., serrated wall) to facilitate improved anchoring.

The implant further includes a plate 130 that is matable with the body 110. Titanium is suitable material for the plate 130. As shown in FIGS. 1 and 2 the plate 130 is mated with the anterior face 116 of the body. However, other embodiments of the fusion implant are configured for mating the plate 130 to the body 110 at locations other than the anterior face 116 as required for the direct lateral approach to the spine.

The plate 130 includes an upper surface 132 lying substantially in the upper plane of the upper surface 112 of the body 110 and a lower surface 134 lying substantially in the lower plane of the lower surface 114 of the body 110. The plate 130 includes a first surface 136 extending substantially perpendicular to the upper and lower surfaces 132, 134 and upper and lower planes, and facing the body 110. It should be appreciated that the upper and lower surfaces 132, 134 of the plate 130 may include gripping members (not shown), such as serrations, grooves, ribs, or teeth, or their surfaces may be roughened in any known manner to facilitate improved anchoring.

Although the plate 130 can be bonded to the body 100 so that the plate and body cannot move with respect to each other via a rigid rivet mechanism, they can also be mated through a modular mechanism allowing the plate 130 to be attached to the body 100 before or after the body has been inserted into the interbody space. For example, in the illustrated embodiment, the plate 130 is bonded through a rivet attachment to the body 100. However, it is envisioned that an additional option would be for the plate 130 to be attached to the body 100 through a threaded screw attachment, a cam and shaft attachment, or a rotational locking tab.

It should be appreciated that in other embodiments, the plate 130 may be embedded in the body 100. For example, an embedded portion (not shown) of the plate 130 may extend from the first surface 136 and be received by the body 100. In some aspects, the body 100 may then be moulded directly to the plate 130 via the embedded portion. In other aspects, the plate 130 may be embedded in the body 100 in any conventional manner.

The plate 130 includes a second surface 138 extending substantially perpendicular to the upper and lower surfaces 132, 134 and upper and lower planes, and facing in a direction opposite to that of the first surface 136 away from the body 110, for example, in an anterior direction upon implantation of the implant 100 intervertebrally.

The plate 130 includes one or more boreholes configured to receive a fastener. Although the illustrated embodiment shows three boreholes, it should be appreciated that other embodiments may include two boreholes or more than three boreholes. As shown in FIGS. 1 and 2, in one aspect of the disclosure, the boreholes include a first fastener whole 142, a second fastener hole 144, and a third fastener hole 146. The first, second, and third fastener holes 142, 144, 146 each have an axis angled from about 25 degrees to about 70 degrees with respect to the horizontal center plane of the implant body 110. In some aspects, the axes of the first, second, and third fastener holes 142, 144, 146 are angled from about 35 degrees to about 50 degrees with respect to the horizontal center plane.

The implant 100 may include a plurality of fasteners 150, 150', and 150" such as, for example, blades. Each fastener 150, 150', 150" may include a head portion 152 and a shank portion 154. The shank portion 154 extends from the head portion 152. The shank portion 154 has a region (not shown) adjacent the head portion 152 with a substantially circular cross section. The shank portion 154 includes a flattened free end 158 opposite the head portion 152. According to various aspects, the shank portion 154 transitions from the circular cross section region to the flattened free end 158 in a substantially continuous manner. In some aspects, the shank portion 154 curves along its length, as shown in FIGS. 1 and 2.

Figure 3:
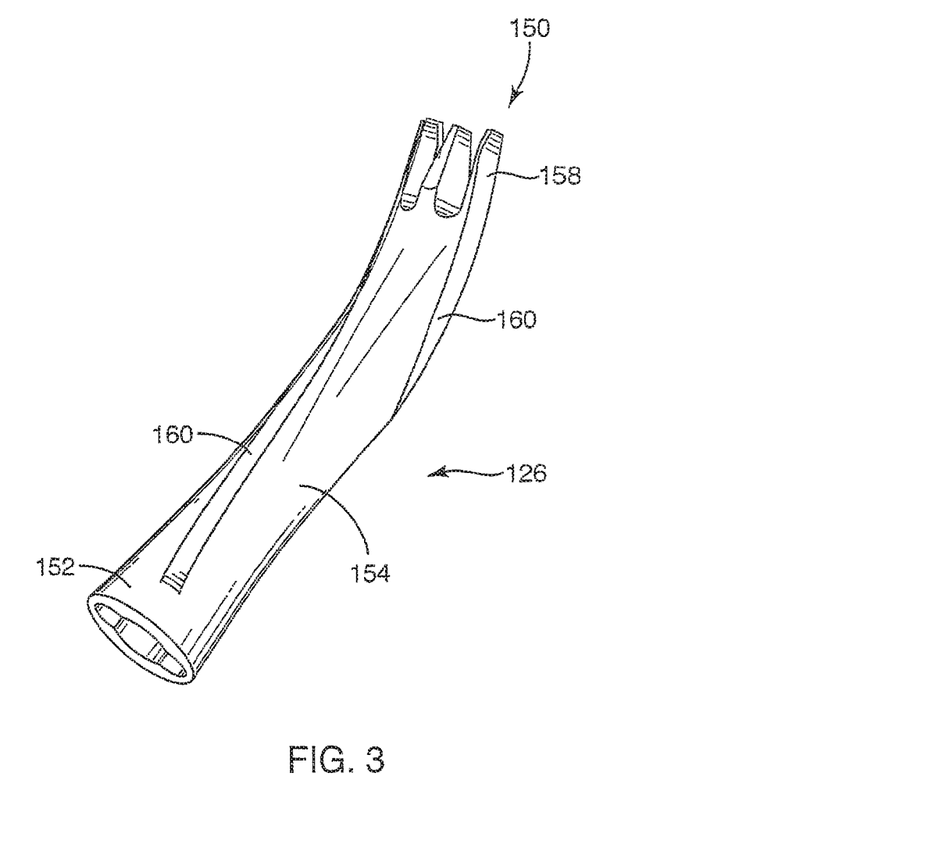
FIG. 3 is a top perspective view of an exemplary fastener in accordance with various aspects of the disclosure.

Referring to FIG. 3 each fastener 150 may include one or more splines 160 arranged helically on the shank portion 154 that facilitate self-tapping into a vertebra. In some aspects, one or more of the fasteners 150 may include two or more splines 160 that commence at different sides, for example, in some aspects diametrically opposite sides, of the circular cross section region 156 of the shank portion 154 and spiraling helically at substantially the same pitch along the length of the shank portion 154 and terminate at opposed sides of the free end 158. In some aspects, the splines 160 wrap around about one quarter of a periphery of the shank portion 154 as the splines 160 extend along the length of the shank portion 154. In some aspects, the splines 160 may extend in a non-spiraling manner along the axis of the shaft.

According to various aspects, the head portion 152 of at least one of the fasteners 150 conically tapers toward the shank portion 154. At least one of the first, second, and third fastener holes 142, 144, 146 has a conical surface (not shown) so as to complement the conical taper of the fasteners. As the fastener hole 142, 144, 146 tapers conically towards its underside, a fastener 150 fitted with a matching conical head may be rigidly anchored in said borehole. In some aspects, the conical fastener hole exhibits a cone angle smaller than the resultant angle of friction. For example, the fastener hole's conicity may be 1:3.75 to 1:20, and in some aspects from 1:5 to 1:15.

Referring again to FIGS. 1 and 2, the first and second fastener holes 142, 144 may be configured to retain the head portion 152 of the first and second fasteners 150', respectively, between the upper and lower planes defined by the upper and lower surfaces 112, 114 of the body 110. A portion 154 of the shank of the first and second fasteners 150' extends from the first and second fastener holes 142, 144 beyond the upper plane. In some aspects, the shank portion 154 of the first and second fasteners may be curved in a direction away from the upper surface 112 of the body 110. The third fastener hole 146 may be configured to retain the head portion 152 of the third fastener 150" between the upper and lower planes defined by the upper and lower surfaces 112, 114 of the body 110. A portion 154 of the shank extends from the third fastener hole 146 beyond the lower plane. The shank portion 154 may be curved in direction away from the lower surface 114 of the body 110. This curved angulation of the shanks relative to the upper and lower surfaces 112, 114 allows for top loading of the spiral blade anchors into their relative vertebral segments into which they are placed for fixation.

The spiral blade fasteners are coupled to the plate through the mated tapered heads. Alternatively, they are locked to the plate via a cover plate or an expanding head, or a locking cap, or a locking tab, or a locking seal, or a locking ring, or a locking lip.

According to some aspects of the disclosure, the upper surface 112 of the body 110 may be at least partially configured to lie adjacent to the endplate of a first vertebra, and the lower surface 114 of the body 110 may be at least partially configured to lie adjacent to the endplate of a second vertebra. In some aspects of the disclosure, the upper surface 112 of the body 110 may be at least partially configured to lie adjacent the lower surface of another intervertebral implant similar in structure to the implant 100 presently described, while the lower surface 114 of the body 110 may be at least partially configured to lie adjacent to the endplate of a second vertebra. In some aspects of the disclosure, the upper surface 112 of the body 110 may be at least partially configured to lie adjacent to the endplate of a first vertebra, while the lower surface 114 of the body 110 may be at least partially configured to lie adjacent the upper surface of another intervertebral implant similar in structure to the implant 100 presently described.

It should be appreciated by persons skilled in the art that the size of the body 100, plate 130, and fasteners 150, 150', 150" may be varied to facilitate implantation at different regions of the spinal column. For example, the length and/or width of the body 100, plate 130, and fasteners 150, 150', 150" may be made smaller for use in the cervical region as compared with the thoracic and lumbar regions. On the other hand, the length and/or width of the body 100, plate 130, and fasteners 150, 150', 150" may be made larger for use in the lumbar region as compared with the thoracic and cervical regions.

It will be apparent to those skilled in the art that various modifications and variations can be made to the intervertebral implants of the present disclosure without departing from the scope of the invention. Throughout the disclosure, use of the terms "a," "an," and "the" may include one or more of the elements to which they refer. Other embodiments of the invention will be apparent to those skilled in the art from consideration of the specification and practice of the invention disclosed herein. It is intended that the specification and examples be considered as exemplary only.

What is claimed and desired to be secured by United States Letters Patent is:

1. A method of securing to a bone, the method comprising:
providing a fastener defining a radial, a circumferential, and an axial direction, the axial direction extending along a curvilinear axis from a head at a proximal end to an insertion point located at a distal end and capable of inserting into the bone, the fastener including the head, insertion point, a shank extending therebetween along the curvilinear axis, splines extending radially away from the curvilinear axis and spiraling therearound with a pitch less than 1 turn per the entirety of the length, thereby rendering the fastener capable of inserting axially along the splines into the bone;
positioning the fastener with the distal end at an entry point selected on the bone;
inserting the distal end into the bone by movement along the axial direction in response to pressing in the axial direction against the head;
directing, by the splines, progress of the fastener into the bone along a helical path cut by the splines about the axial direction in response to the pressing; and
securing, by the splines, the fastener against movement directly toward the entry point.

2. The method of claim 1, comprising:
providing a body provided with at least one aperture sized and shaped to receive the fastener; and
inserting the body between the bone and the fastener to initially orient the fastener for entry into the bone.

3. The method of claim 2, wherein the splines are oriented proximate the distal end to resist movement directly toward the insertion point.

4. The method of claim 3, wherein the axis at the distal end is oriented at an angle of from about 50 degrees to about 90 degrees with respect to the axis at the head.

5. The method of claim 1, comprising press-driving the fastener along the axial direction into the bone.

6. The method of claim 5, wherein an angle between the axis at the head and the axis proximate the distal end represent a "terminal angulation" selected to resist pullout and rotation of the fastener after the insertion.

7. An apparatus operable as a fastener anchoring to a bone, the apparatus comprising:
a curvilinear axis defining a radial direction, circumferential direction, and axial direction along the curvilinear axis;
a head defining a proximal end of the fastener;
a distal end of the fastener, defining a length along the curvilinear axis and constituting a penetrator region capable of initiating penetrating of the bone in the axial direction in response to pressing the head along the axial direction;
a shank extending continuously between the head and the distal end and comprising splines, each spline extending radially away from the axis while extending axially therealong to define a helical path having a pitch greater than the length, per one circumferential progression of the spline.

8. The apparatus of claim 7, wherein the pitch is greater than double the length per one circumferential progression of the splines.

9. The apparatus of claim 8, wherein the pitch approaches about four times the length per single circumferential progression of the splines.

10. The apparatus of claim 7, wherein the splines define a constant diameter of the shank for at least a portion of the length.

11. The apparatus of claim 10, wherein the splines define a constant diameter between the head and the penetrator region.

12. A method of anchoring to bone, the method comprising:
providing a fastener defining radial, circumferential, and axial directions, substantially mutually orthogonal, the axial direction extending along an axis, curvilinear and defining a length therealong, the fastener comprising a head at a proximal end of thereof, an insertion point at a distal end thereof and capable of penetrating the bone without rotational force imposed thereon, and a shank extending between the head and the insertion point to include splines, the splines extending radially to a diameter constant along the shank and axially along a helical trajectory about the axis at a pitch per helical rotation greater than the length, rendering the fastener capable of inserting axially along the splines into the bone while self-rotating along the helical path of the splines in response to force applied axially to the head;
positioning the insertion point at an entry point selected on the bone;
inserting the distal end into the bone by pressing in the axial direction against the head;
directing, by the splines, progress of the fastener into the bone along the helical path guided by the splines in response to the inserting.

13. The method of claim 12, comprising securing, by the splines, the fastener against movement directly toward the entry point and against simple rotation about the head in all directions.

14. The method of claim 12, wherein the axis at the insertion point is oriented in a first direction with respect to the bone before the pressing, and the axis at the head is oriented in the first direction following completion of insertion of the fastener.

15. The method of claim 12, wherein the splines proximate the distal end are oriented to resist movement directly toward the entry point.

16. The method of claim 12, comprising:
positioning a body between the bone and an adjacent bone, the body being provided with at least one aperture sized and shaped to receive therethrough the fastener;
inserting the fastener through the body and into the bone; and
inserting another fastener through the body into the adjacent bone to provide fixation and stability between the bone and the adjacent bone.

17. The method of claim 12, comprising press-driving the fastener along the axial direction into the bone.

18. The method of claim 12, wherein an angle between the axis at the head and the axis proximate the distal end represent a "terminal angulation" selected to resist pullout and resist rotation of the fastener after the insertion.

19. The method of claim 12, comprising positioning a structure between the bone and the fastener before the inserting.

20. The method of claim 12, wherein the structure comprises a body capable of receiving the fastener and gripping against the bone in response to compression imposed thereon by the head.

* * * * *